(12) United States Patent
Inoue et al.

(10) Patent No.: US 6,320,096 B1
(45) Date of Patent: Nov. 20, 2001

(54) DISPOSABLE TRAINING PANTS FOR INFANTS WITH WETNESS INDICATOR

(75) Inventors: Yasushi Inoue; Toshifumi Otsubo, both of Kagawa-ken (JP)

(73) Assignee: Uni-Charm Corporation, Ehime-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/028,057

(22) Filed: Feb. 23, 1998

(30) Foreign Application Priority Data

Feb. 28, 1997 (JP) ..................................... 9-046775

(51) Int. Cl.⁷ ....................................................... A61F 13/15
(52) U.S. Cl. ...................................... 604/378; 604/385.08
(58) Field of Search ................................ 604/385.1, 381, 604/382, 378, 385.01, 385.08, 385.23

(56) References Cited

U.S. PATENT DOCUMENTS

| 5,431,643 | * | 7/1995 | Ouellette et al. | ................. 604/385.1 |
| 5,743,776 | * | 4/1998 | Igaue et al. | .......................... 442/414 |

FOREIGN PATENT DOCUMENTS

| 0 615 738 | | 9/1994 | (EP) . | |
| 0 661 031 | | 7/1995 | (EP) . | |
| 2081098 | * | 2/1982 | (GB) | ................................... 604/381 |
| WO96/12459 | | 5/1996 | (WO) . | |

* cited by examiner

Primary Examiner—Dennis Ruhl
(74) Attorney, Agent, or Firm—Lowe Hauptman Gilman & Berner, LLP

(57) ABSTRACT

Disposable training pants includes a liquid-permeable topsheet layer, a liquid-impermeable backsheet layer and a liquid-absorbent core disposed therebetween. The topsheet layer is formed in a transverse middle thereof overlying at least a crotch region of the pants with a liquid-impermeable zone having a hydrophobicity higher than the laterally adjacent zones.

4 Claims, 3 Drawing Sheets

DISPOSABLE TRAINING PANTS FOR INFANTS WITH WETNESS INDICATOR

BACKGROUND OF THE INVENTION

This invention relates to disposable training pants used to wean infants from diapers.

Japanese Utility Model Application Laid-Open (Kokai) No. Hei7-33916 discloses training pants for infants, in which a topsheet of the pants is provided on an upper surface thereof with wetness indicator means having a water hold capacity per unit area higher than that of the topsheet itself.

However, it is difficult for the training pants of the prior art to provide the pants wearer with an uncomfortable feeling of wetness unless the wetness indicator means is adequately wetted. In other words, the wetness indicator means cannot satisfactorily function when an amount of discharged urine, i.e., an amount of urine held in the wetness indicator means, is relatively small.

SUMMARY OF THE INVENTION

In view of the problem as has been described above, it is a principal object of the invention to provide improved training pants that gives a wearer a significant feeling of wetness even when an amount of discharged urine is relatively small.

The object set forth above is achieved, according to the invention, by disposable training pants comprising a liquid-permeable topsheet layer, a liquid-impermeable backsheet layer and a liquid-absorbent core disposed between these two sheet layers and having a front waist region, a rear waist region and a crotch region extending between the front and rear waist regions. The topsheet layer is formed in a transverse middle thereof at least in the crotch region with a liquid-impermeable zone having a hydrophobicity higher than laterally opposite side zones adjacent the middle zone.

The laterally opposite side zones may be either hydrophilic or liquid-permeable and hydrophilic.

According to an alternative embodiment, the topsheet layer entirely covers the absorbent core and comprises a liquid-permeable and slightly hydrophobic or hydrophilic first sheet and a liquid-impermeable and highly hydrophobic second sheet placed on an upper surface of the first sheet in a transverse middle thereof and indirectly covering the absorbent core partially in a transverse direction thereof.

The second sheet may comprise a liquid-impermeable and highly hydrophobic zone in a transverse middle of the second sheet and hydrophilic zones extending on both sides of the liquid-impermeable and highly hydrophobic zone.

According to still another embodiment, the second sheet comprises highly hydrophobic zones and slightly hydrophobic or hydrophilic zones alternately arranged transversely of the absorbent core.

DESCRIPTION OF THE PREFERRED EMBODIMENTS

Figure 1:
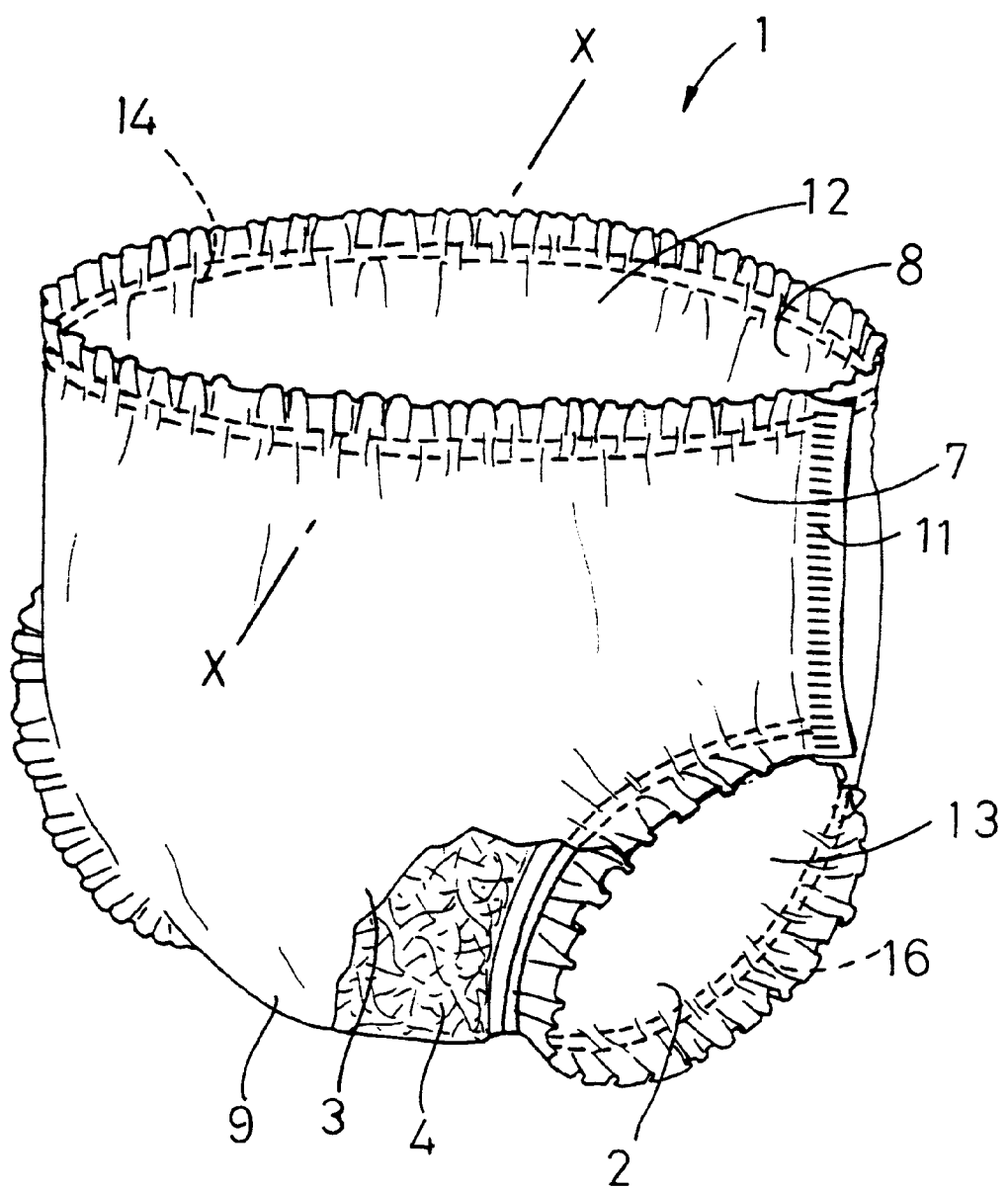
FIG. 1 is a perspective view of training pants for infants according to the invention as partially broken away.

Training pants 1 shown in FIG. 1 comprises a liquid-permeable topsheet layer 2, a liquid-impermeable backsheet layer 3 and a liquid-absorbent core 4 disposed between these two sheet layers 2, 3. The pants 1 has a front waist region 7, a rear waist region 8 and a crotch region 9 extending between the front and rear waist regions. The front and rear waist regions 7, 8 are put flat together and bonded together along transversely opposite sides of the pants 1. Bonding of these two waist regions along each side edge of the pants 1 is carried out at spots 11 arranged intermittently in the vertical direction. The pants 1 additionally has a waist-opening 12 and a pair of leg-openings 13. These openings 12, 13 are provided along their peripheral edges with elastic members 14, 16 which are bonded under appropriate tensions to an inner surface of the topsheet layer 2 and/or the backsheet layer 3.

Figure 2:
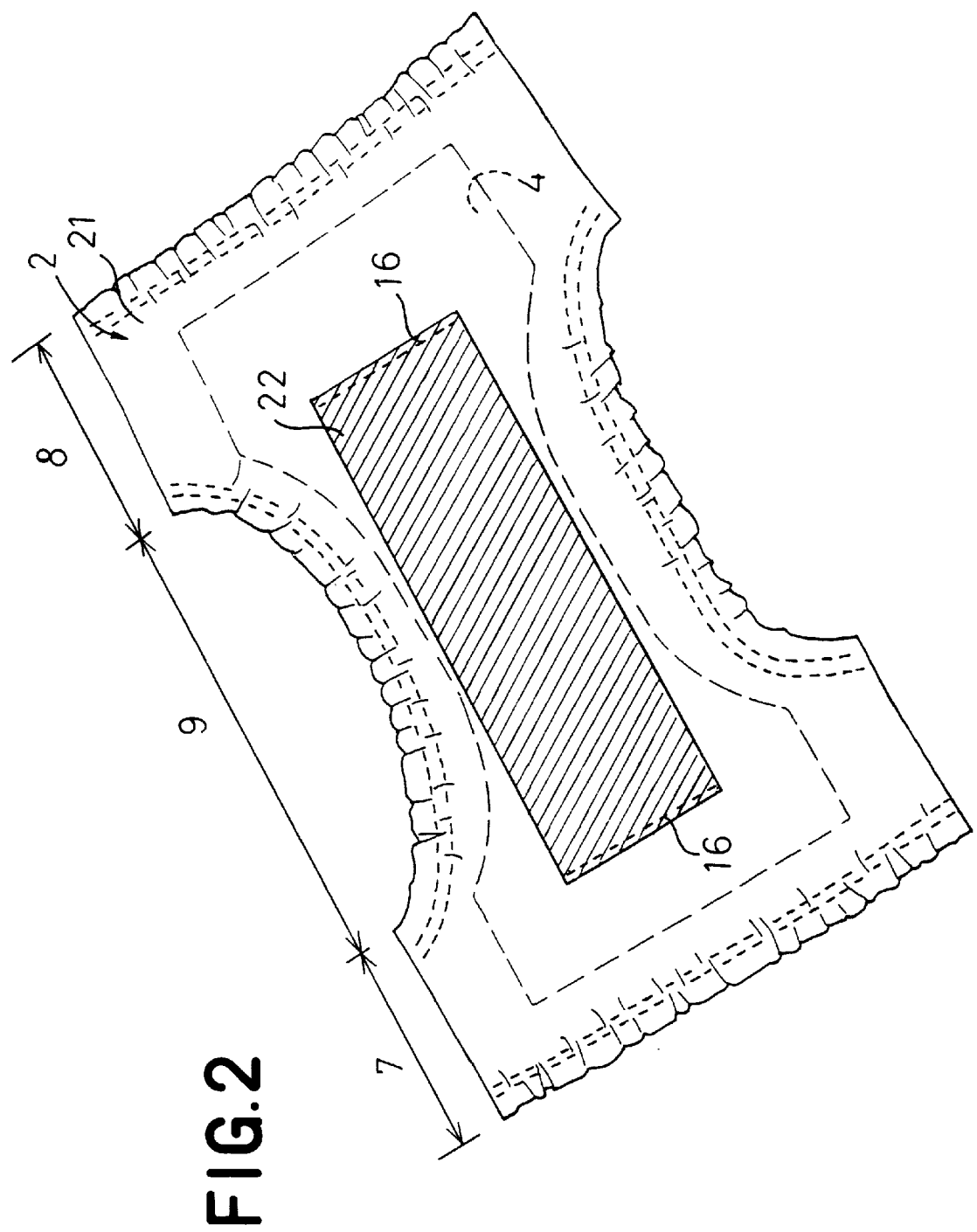
FIG. 2 is a perspective view showing the same training pants as unfolded longitudinally thereof.

FIG. 2 is a perspective view showing the same pants with the front and rear waist regions 7, 8 bonded together having been peeled off from each other and unfolded in a direction indicated by X—X, as partially broken away. As shown, the pants 1 in this state presents a substantial hourglass-shape. The topsheet layer 2 of the pants 1 comprises a liquid-permeable first sheet 21 which is identical to the backsheet layer 3 both in shape and in size and a hydrophobic second sheet 22 arranged in a transverse middle of the first sheet 21 so as to extend longitudinally across the crotch region 9 into the front and rear waist regions 7, 8. The second sheet 22 has a lower surface thereof bonded to an upper surface of the first sheet 21 along bonding lines 16 defined by longitudinally opposite ends. Between these two bonding lines 16, the first and second sheets 21, 22 may be intermittently bonded to each other or may not be bonded at all.

The first sheet 21 is a liquid-permeable sheet entirely covering an upper surface of the absorbent core 4 and may be made of a nonwoven fabric obtained from staple fibers of thermoplastic synthetic resin, a thermoplastic synthetic resin film having a plurality of liquid-permeable apertures, or a thermoplastic synthetic resin film having a plurality of openings from peripheral edges of which liquid passages or tubes extend toward the absorbent core 4. While these nonwoven fabric and film are of hydrophobic nature, it is possible to mix or laminate hydrophilic natural fibers on the nonwoven fabric at a ratio of 5–40% by weight and thereby to make the first sheet more or less hydrophilic. It is also possible to employ the nonwoven fabric or film previously treated with a suitable hydrophilicity enhancing agent. A basic weight of the nonwoven fabric is preferably 10–100 g/m$^2$ and a thickness of the film is preferably 0.02–0.1 mm.

The second sheet 22 is a sheet indirectly covering the upper surface of the absorbent core 4 with the first sheet 21 interposed therebetween. The second sheet 22 has a width narrower than the width of the absorbent core 4 and, in the crotch region 9, lies 7 mm or more inward from transversely opposite sides of the absorbent core 4. The second sheet 22 may be made of a nonwoven fabric formed by staple fibers or melt blown fibers of thermoplastic synthetic resin, a thermoplastic synthetic resin film or thermoplastic synthetic resin film having a plurality of liquid-impermeable apertures. In any case, the second sheet 22 should be a liquid-impermeable sheet having a hydrophobicity higher than that of the first sheet 21. Such liquid-impermeability of the second sheet 22 means that an amount of urine discharged onto an upper surface of the second sheet 22 placed upon the first sheet 21 cannot easily transfer through the second sheet 22 itself or through the apertures formed in the second sheet 22 to the first sheet 21. The amount of urine discharged onto the second sheet 22 stagnates on the second sheet 22 practically without being absorbed thereby or partially flows outward beyond transversely opposite side edges of the second sheet 22, then permeates the first sheet 21 and is finally absorbed by the absorbent core 4, since the second sheet 22 has a high hydrophobicity and liquid-impermeability. Such second sheet 22 may be formed by a hydrophobic nonwoven fabric or film with or without repellency treatment. When the nonwoven fabric is employed, a web, for example, having a fineness of 0.05–7 d and a basic weight of 10–100 g/m$^2$ may be appropriately compression-molded to increase a fiber density thereof and thereby to make it liquid-impermeable.

With the training pants 1 constructed as has been described, a pants wearer can perceive a significant wetness, since most of the urine discharged on the second sheet 22 stagnates thereon. When an amount of discharged urine is relatively large and flows outward beyond the side edges of the second sheet 22, the amount of urine flowing outward beyond the side edges of the second sheet 22 is reliably absorbed by the absorbent core 4 without leaking outwardly of the pants 1. This is the reason that the second sheet 22 has a width narrower than that of the absorbent core 4, i.e., the absorbent core extends outward beyond the side edges of the second sheet 22.

Figure 3:
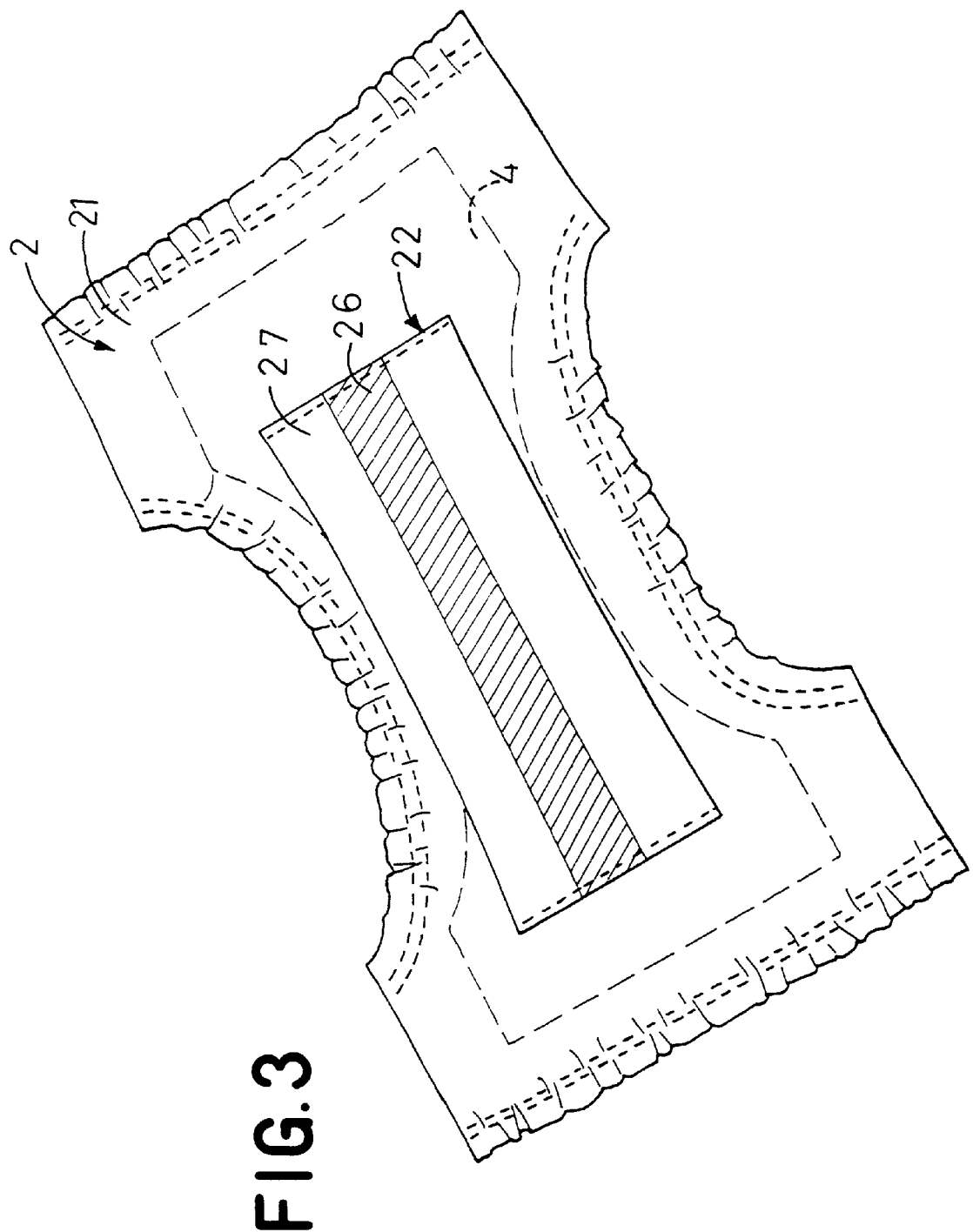
FIG. 3 is a view similar to FIG. 2 showing a variant of the invention.

FIG. 3 is a view similar to FIG. 2 showing a variant of the invention. According to this variant, the second sheet 22 of the pants 1 comprises a liquid-impermeable and highly hydrophobic first wetness telling zone 26 lying in a transverse middle thereof and a pair of hydrophilic second wetness telling zones 27 on both sides of the first telling zone 26. The first wetness telling zone 26 provides a pants wearer with a significant feeling of wetness as the second sheet 22 does in the case of the embodiment shown by FIG. 2. Such wetness telling function is achieved also by the second wetness telling zone 27 since the zone 27 can absorptively hold an adequate amount of urine. In the second sheet 22, the first wetness telling zone 26 is dimensioned to have a width narrower than that of the absorbent core 4. When the liquid-permeable second wetness telling zones 27 are employed, a full width of the second sheet 22 can be dimensioned to be larger than the width of the absorbent core 4. Such second sheet 22 can be obtained by treating transversely opposite side portions of a liquid-impermeable and highly hydrophobic nonwoven fabric with a suitable hydrophilicity enhancing agent and forming these portions with liquid-permeable apertures.

Even when a relatively large amount of urine is discharged, urine leakage is effectively prevented by the pants 1 of FIG. 3, since an amount of urine flowing transversely of the pants 1 is caught by the second wetness telling zones 27, then permeates the first sheet 21 and is absorbed by the absorbent core 4. In the case of the pants shown by FIG. 2, if the first sheet 21 is hydrophilic, such hydrophilic first sheet 21 lying outside the second sheet 22 can provide the same function as the second wetness telling zones 27 in FIG. 3 to give a pants wearer a feeling of wetness. However, the embodiment shown by FIG. 2 is accompanied with an apprehension that the second wetness telling zone (the first sheet 21) might not come in contact with a wearer's skin since there is a level difference between the first wetness telling zone (the second sheet 22) and the second wetness telling zone (the first sheet 21). In the case shown by FIG. 3, on the other hand, the first and second wetness telling zones 26, 27 are defined by a single sheet without any level difference therebetween. Therefore, these two telling zones 26, 27 always come in contact with a wearer's skin as a single sheet so that the second telling zones 27 also can effectively give a pants wearer a significant feeling of wetness. The second sheet 22 shown by FIG. 3 may comprise the first wetness telling zone 21 and the second wetness telling zone 22 alternately arranged transversely of the sheet 22 so far as the outermost first wetness telling zones 26 lie preferably 7 mm or more inward of the transversely opposite side edges of the absorbent core 4.

It is possible without departing from the spirit and the scope of the invention to employ a single liquid-impermeable sheet to form the topsheet layer 2. In this case, this single sheet is formed in a transverse middle thereof with a highly hydrophobic zone and on a transversely opposite side portions thereof with a plurality of a liquid-permeable pores. However, the embodiment shown by FIGS. 1 and 2 is preferred to the embodiment shown by FIG. 3 from the viewpoint of a manufacturing cost of the training pants.

The backsheet layer 3 of the training pants 1 according to the invention may be made of a liquid-impermeable or breathable and liquid-impermeable thermoplastic synthetic resin film or such film on which a nonwoven fabric has been laminated to obtain a cloth-like touch. The liquid-absorbent core 4 may be made of fluff pulp fibers or a mixture of such fluff pulp and polymer particle of high water absorptivity. Bonding of various components constituting the pants 1 may be achieved by use of any suitable adhesive agent such as hot melt adhesive or by heat-sealing of the component themselves.

With the training pants according to the invention, the topsheet layer of the pants is formed in the middle of the crotch region with the liquid-impermeable and highly hydrophobic zone. In consequence, most of the urine discharged onto the topsheet layer of the pants stagnates thereon without being absorbed and give a pants wearer a significant uncomfortable feeling of wetness.

With the embodiment in which there are provided adjacent the liquid-impermeable and highly hydrophobic zone with the hydrophilic zones, an amount of urine flowing transversely of the pants is caught by the hydrophilic zones to prevent any amount of urine from leaking aside. Simultaneously, the hydrophilic zones also contribute to give a pants wearer a feeling of wetness.

With the embodiment in which the liquid-impermeable and highly hydrophobic zone has a width narrower than that of the absorbent core and there are provided on both sides of the zone with the liquid-permeable zones, an amount of urine flowing transversely of the pants permeates the liquid-permeable zones and is absorbed by the liquid-absorbent core. In this manner, leaking aside of urine is reliably avoided.

What is claimed is:

1. A disposable training pants comprising a top sheet layer, a liquid impermeable back sheet layer and a liquid absorbent core disposed between said top sheet layer and back sheet layer to jointly define a front waist region, a rear waist region and a crotch region extending between said front and rear waist regions, wherein the top sheet layer further includes a second sheet placed on an upper surface of the top sheet in a middle zone thereof and indirectly covering the absorbent core partially in a direction transverse said front and rear waist regions, wherein the second sheet comprises a liquid impermeable and highly hydrophobic zone in a middle zone of the second sheet and hydrophilic zones on the second sheet and respectively extending on both sides of the liquid impermeable and highly hydrophobic zone.

2. The training pants according to claim 1, wherein a width of said second sheet is larger than the width of the absorbent core.

3. The training pants according to claim 1, wherein longitudinally extending sides of said liquid impermeable and highly hydrophobic zone in said middle zone of said second sheet are located inward of the corresponding longitudinal side edges of the absorbent core by a distance of at least 7 mm.

4. The training pants according to claim 1, wherein said middle zone of said second sheet is sufficiently liquid-impermeable so that urine stagnates thereon to provide the pants wearer with a significant feeling of wetness.

* * * * *